United States Patent
Place et al.

(10) Patent No.: US 6,657,066 B1
(45) Date of Patent: Dec. 2, 2003

(54) SYNTHESIS OF CERTAIN TRIAZOLE COMPOUNDS

(75) Inventors: Ileana Place, Webster, NY (US); John W. Harder, Rochester, NY (US); Robert F. Romanet, Rochester, NY (US); William B. Vreeland, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/315,631

(22) Filed: Dec. 10, 2002

(51) Int. Cl.⁷ ............................................. C07D 487/04

(52) U.S. Cl. .................................... 548/262.4

(58) Field of Search ...................... 548/262.4

(56) References Cited

U.S. PATENT DOCUMENTS

| 4,540,654 A | 9/1985 | Sato et al. |
| 5,378,587 A | 1/1995 | Krishnamurthy et al. |

FOREIGN PATENT DOCUMENTS

| EP | 0 119 860 | 10/1989 |

*Primary Examiner*—Patricia L. Morris
(74) *Attorney, Agent, or Firm*—Arthur E. Kluegel

(57) ABSTRACT

Disclosed is a process for forming a 1H-pyrazolo (1,5-b)-[1,2,4]-triazole compound by ring closing a pyrazoloamidine compound comprising reacting the amidine with an oxidizing agent having a reduction potential vs Ag/AgCl that is more positive than −0.16V and less than +1.43V in the presence of a halogen atom. The invention also discloses certain triazole compounds that are successfully made by the conventional process. The process and compounds of the invention provide improved yields and reduce or eliminate unwanted side-reactions.

22 Claims, No Drawings

SYNTHESIS OF CERTAIN TRIAZOLE COMPOUNDS

FIELD OF THE INVENTION

This invention relates to pyrazolotriazole compounds and a process for preparing them employing certain oxidant/halogen containing materials.

BACKGROUND OF THE INVENTION

One of the useful classes of dyes is one based on a 1H-pyrazolo (1,5-b)-[1,2,4]-triazole compound. These dyes are desirable because they have a spectral absorption curve that has a relatively narrow half-bandwidth and because they can typically be stabilized to provide a very useful half-life. Such dyes of the aza-methine type typically have a hue in the 500–600 nm range although with judicious selection of the substituents it is possible to shift the maximum absorption outside that range.

One notable use for such dyes is in photographic imaging, particularly silver halide imaging. In such imaging, 1H-pyrazolo (1,5-b)-[1,2,4]-triazole coupler compounds having a leaving group are imagewise converted to the desired dye by a coupling reaction with an oxidized developer, typically a p-phenylene diamine, to form the corresponding dye. The use of such couplers and dyes is detailed In U.S. Pat. Nos. 4,540,654 and 4,621,046.

While such couplers have been found advantageous, the methods of synthesizing them could be improved on. One scheme disclosed for preparing the described triazole couplers is set forth in U.S. Pat. No. 5,378,587. It includes oxamination of the corresponding amidine to form the oxime, sulfonating to form the sulfonate, and heating to ring close and form the desired pyrazolotriazole. Although, this reaction is effective, it requires 3 steps to arrive at the desired product from the amidine.

One method for accomplishing the desired conversion is taught in EP 119,860. This method employs direct oxidation of the imidate to the desired triazole using a lead tetraacetate as an oxidizing agent. When this method was employed in Synthesis Example 11, the reaction provided a yield of only 5.7%. Yields this low are not usually of commercial significance. Higher yields of at least 15% and more desirably at least 40 or even 70% are desired. Yield is important especially when a sequence of reactions is employed, each of which has a yield factor, the combination of which can make the overall yield excessively low.

It is a problem to be solved to provide an alternative means for preparing a 1H-pyrazolo (1,5-b)-[1,2,4]-triazole compound from the corresponding imidate which can be accomplished with less than three steps and results in desirably high yields.

SUMMARY OF THE INVENTION

The invention provides a process for forming a 1H-pyrazolo (1,5-b)-[1,2,4]-triazole compound by ring closing a pyrazoloamidine compound comprising reacting the amidine with an oxidizing agent having a reduction potential vs Ag/AgCl that is more positive than −0.16V and less than +1.43V in the presence of a halogen atom. The invention also provides certain triazole compounds that are not successfully made by the conventional process.

The process and compound of the invention provide improved yields and reduce or eliminate unwanted side-reactions.

DETAILED DESCRIPTION OF THE INVENTION

The invention is summarized above.

The halogen employed in the reaction may either be part of the oxidizing agent or part of a separate compound from the oxidizing agent. The reduction potential vs. Ag/AgCl is more positive than −0.16 and less than +1.43 and is desirably more positive than 0 and less than 1.3. Suitably, the range of potentials is from 0 to 1.1, and typically from 0.1 to 1.0. The reduction potential is measured in the conventional manner vs. Ag/AgCl.

The oxidizing agent is selected from any of those that provide the desired reduction potential. Suitable ones include those selected from the group consisting of halogens, chloro, bromo, or iodoamides, chloro, bromo or iodoimides, hypervalent iodine compounds, perhalogen compounds, peroxide/halide combinations, sulfonyl halides, halo-hydantoins and N-halo compounds.

Examples of halogen containing oxidants and their corresponding redox potentials are as shown in Table I:

TABLE I

| Oxidant | Redox Potential | Ref. Electrode | Type |
|---|---|---|---|
| DCDMH** N,N-dichloro-dimethylhydantoin | −0.2 V | " | Comparative |
| NCS*** N-chlorosuccinimide | −0.16 V | " | " |
| Lead Tetraacetate* | 1.43 V | Ag/AgCl | " |
| Iodobenzene-bis-trifluoroacetate*§ | 0.06 to 1.0 V | " | Invention |
| Iodobenzene diacetate*§ | 0.06 to 1.0 V | " | " |
| Hydroxytosyloxy-iodobenzene*§ | 0.06 to 1.0 V | " | " |
| DBDMH** N,N-dibromo-dimethylhydantoin | 0.4 V | " | " |
| $Br_2$* | 0.88 V | " | " |
| $Cl_2$* | 1.16 V | " | " |

*http://library.thinkquest.org/3659/reference/reductionpotentials.html?tqskip1=1&tqtime=0710
**U.S. Pat. No. 5,972,864
***Lind, J.; Jonsson, M.; Erikson, T. E., Merenyi, G. J. Phys. Chem., 1993, 97, 1610–1614
§The range of +0.06 to 1.0 V is estimated taking into consideration the data of iodine oxidation given in the reference*

Specific examples of oxidizing agent/halogen combinations useful in the invention are:

$Cl_2$     1

$Br_2$     2

$I_2$     3

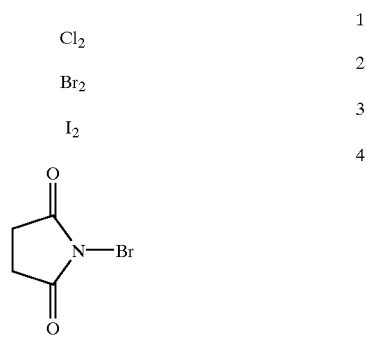

4

5
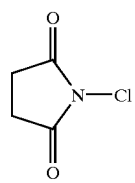
6
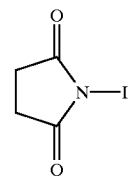
7
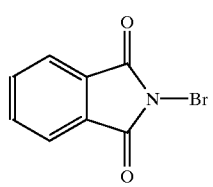
8
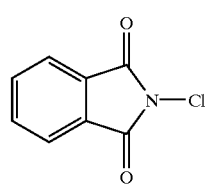
9
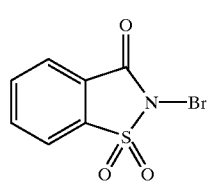
10
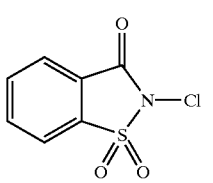
11
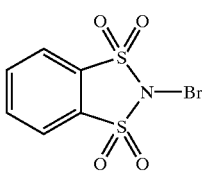
12
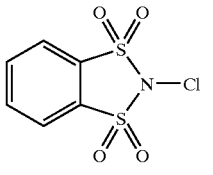
13
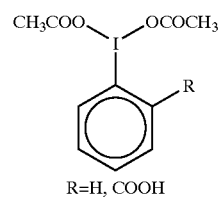
R=H, COOH
14
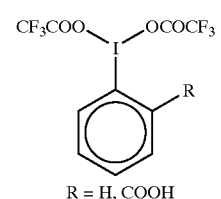
R = H, COOH
15
NaOCl + HCl
16
NaOBr + HCl
17
NaOCl + HBr
18
$H_2O_2$ + HCl
19
$H_2O_2$ + KBr
20
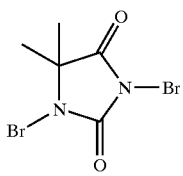
21
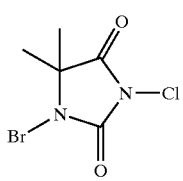
22
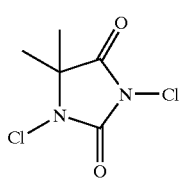
23
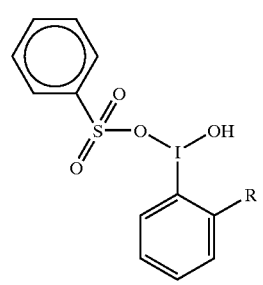
R = H, COOH -continued

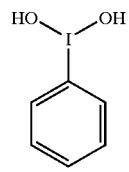

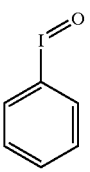

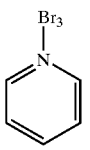

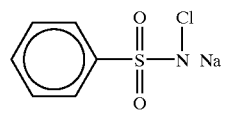

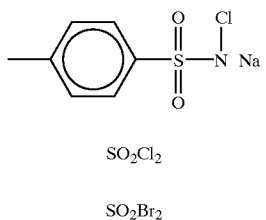

SO₂Cl₂

SO₂Br₂

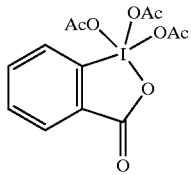

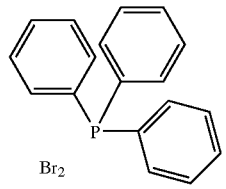

The inventive process for forming a 1H-pyrazolo (1,5-b)-[1,2,4]-triazole compound by ring closing a pyrazoloamidine is shown in the following equation:

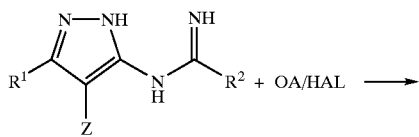

-continued

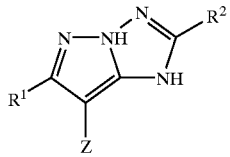

wherein,

R¹ and R² are independently selected alkyl or aryl groups;

Z is H or a substituent; and

OA/HAL represents an oxidizing agent that contains a halogen or a combination of an oxidizing agent and a halogen containing compound, the oxidizing agent having a reduction potential vs Ag/AgCl that is more positive than −0.2V and less than +1.7V.

Z is conveniently Cl. R¹ is desirably a tertiary carbon atom such as a t-butyl group. R² is suitably a substituted alkyl or aryl group containing at least 8 carbon atoms.

The oxidation reaction is suitably carried out at a temperature of from 15 to 150° C., and usually at a temperature of from 60 to 100° C. The reactants are desirably brought together in an aprotic solvent such as an aprotic solvent that is basic, such as one selected from the group consisting of dimethyl formamide, dimethyl acetamide, pyridine, butyronitrile, chlorobenzene, nitrobenzene, 1,2-dichloroethane, toluene, acetic acid, dioxane, ethylene glycol dimethyl ether, and N-methylpyrrolidone.

It is observed that the oxidation step transforms the amidine to the pyrazolotriazole coupler in one step compared to the three steps in the prior art process. As will be shown in the examples that follow, it will provide superior yields of the desired product. Further, it enables the production of triazole compounds that could not be successfully made by the oxime route since the inventive route serves to reduce or eliminate undesired side-reactions.

Compounds that may be made by the process of the invention but not by the conventional process of oxamination are 1H-pyrazolo (1,5-b)-[1,2,4]-triazole compounds containing an anionic leaving group γ to the 2-position of the triazole. Examples of such groups are —Cl, —Br, —I, —OR, and —SO₂OR, where R is a substituent, particularly those compounds where at least one alkyl substituent on the α carbon.

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t- butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo- 1 -oxazolidinyl, 3-dodecyl-2,5-dioxo-1-imidazolyl, and N-acetyl-N-dodecylamino, ethoxycarbonylarnino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbarnoyl, N-methyl-N-tetradecylcarbanoyl, and N,N-dioctylcarbanoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecy-loxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided.

The compounds synthesized in accordance with the invention are useful as coupler intermediates for the formation of dyes such as in the coloring and imaging arts.

The entire contents of the patents and other publications referred to in this specification are incorporated herein by reference.

EXAMPLES

Example 1.

The process of the invention is carried out as follows:

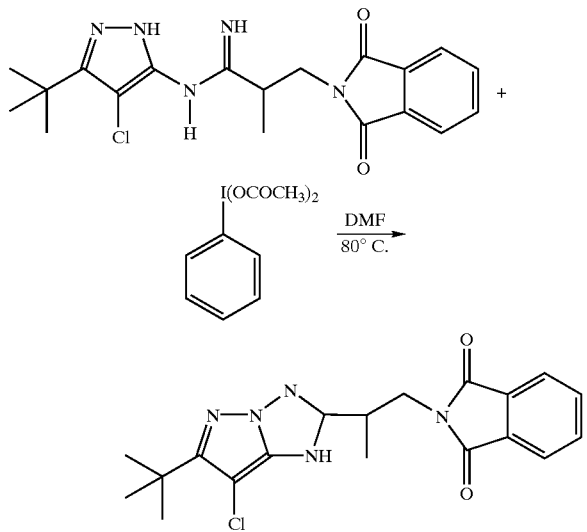

10 g (0.0257 moles) of amidine were dissolved in 50 ml dimethyl formamide and stirred it at room temperature, while adding 33.19 g (0.103 moles) of iodobenzene diacetate (reduction potential about 0.6V) to the reaction mixture. The reaction mixture was heated at 80° C. for 8 hours until the reaction was complete. Work up of the reaction mixture was accomplished by drowning it in water, extracting it in ethyl acetate, drying the ethyl acetate layer over magnesium sulfate, and then using the rotatory evaporator to remove the solvent. The crude product was purified by column chromatography on silica gel using a gradient of 30–50% ethyl acetate to heptane. 5.5 g (55% yield) of pure product was obtained after chromatography.

Example 2.

The same compound is alternatively prepared in accordance with the invention as follows:

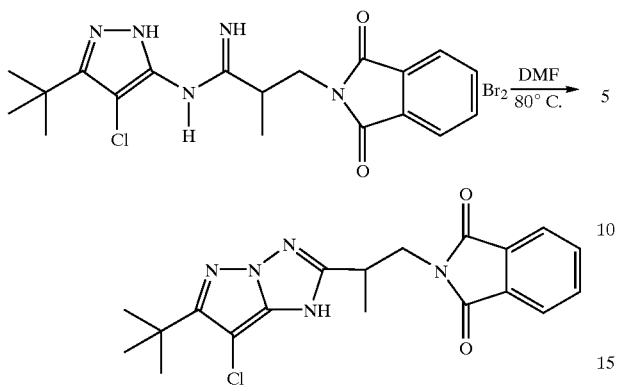

7.8 g (0.02 moles) of amidine was dissolved in 50 ml dimethyl formamide and stirred at room temperature, while adding 6.4 g (0.04 moles) of liquid bromine (reduction potential 0.88V) to the reaction mixture. The reaction mixture was heated at 80° C. for 40 minutes, when reaction was complete. The product was worked up by drowning it in water and extracting it in ethyl acetate, drying the ethyl acetate layer over magnesium sulfate and then using the rotatory evaporator to remove the solvent. The crude product was purified by column chromatography on silica gel using a gradient of 10–40% ethyl acetate to heptane to obtain 6.0 g (77% yield) of pure product after chromatography.

Example 3.

A further inventive alternative is carried out as follows:

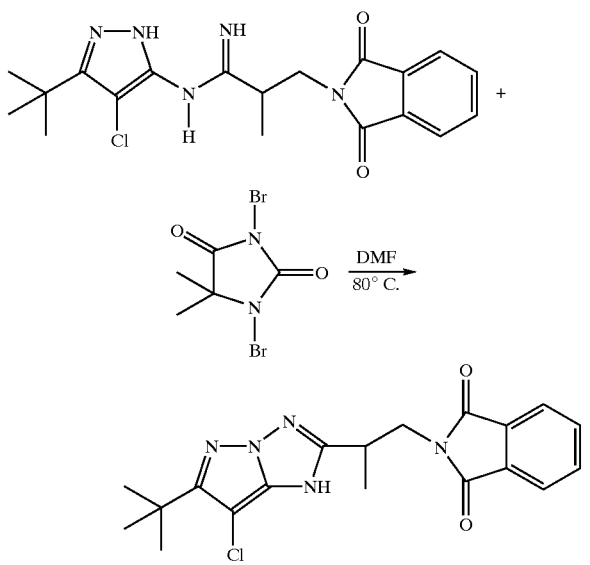

7.8 g (0.02 moles) of amidine were dissolved in 50 ml dimethyl formamide and stirred it at room temperature, while adding 5.7 g (0.02 moles) of 1,3-dibromo 5,5-dimethylhydantoin (reduction potential of 0.4V) to the reaction mixture. The reaction mixture was heated at 80° C. for 60 minutes, when reaction was complete. The reaction mixture was worked up by drowning it in water and extracting it in ethyl acetate, drying the ethyl acetate layer over magnesium sulfate and then using the rotatory evaporator to remove the solvent. The crude product was purified by column chromatography on silica gel using a gradient of 30–50% ethyl acetate to heptane. 3.3 g (42% yield) of pure product were obtained after chromatography.

Example 4.

Several experiments with different oxidizing agents for this ring closure were set-up in parallel overnight. The amidine was that used for Example 3, above and the reaction was conducted at 80° C. The other reagents and the results are as summarized in Table II.

TABLE II

| Sample | Type | Oxidizing Agent | Solvent | Yield-wt % |
|---|---|---|---|---|
| 1 | Invention | iodobenzenediacetate | DMF | 55 |
| 2 | Invention | Br$_2$ | " | 77 |
| 3 | Invention | N,N-dibromo-dimethylhydantoin | " | 42 |
| 4 | Comp | SOCl$_2$ | " | No product |
| 5 | Invention | SO$_2$Cl$_2$ | " | 17 |
| 6 | Invention | (CF$_3$COO)$_2$IC$_6$H$_5$ | " | 64 |
| 7 | Invention | hydroxytosyloxy-iodoC$_6$H$_5$ | " | 30 |
| 8 | Comp | Lead Tetraacetate | " | 12 |
| 9 | Comp | F3Cl$_3$.6H$_2$O | MeOH | No product |
| 10 | Comp | FeCl$_3$ | " | No product |

As the table shows, desirable yields above 15 wt % were obtained with halogen containing oxidizing agents having a redox potential above.

The entire contents of the patents and other publications referred to in this specification are incorporated herein by reference.

What is claimed is:

1. A process for forming a 1H-pyrazolo (1,5-b)-[1,2,4]-triazole compound by ring closing a pyrazoloamidine compound comprising reacting the amidine with an oxidizing agent having a reduction potential vs Ag/AgCl that is more positive than −0.16V and less than +1.43V in the presence of a halogen atom.

2. The process of claim 1 wherein the halogen is a part of the oxidizing agent.

3. The process of claim 1 wherein the halogen is part of a separate compound from the oxidizing agent.

4. The process of claim 1 wherein the reduction potential is less than 1.3.

5. The process of claim 1 wherein the reduction potential is more positive than 0.

6. The process of claim 1 wherein the reduction potential from 0 to 1.1.

7. The process of claim 1 wherein the reduction potential is from 0.1 to 1.0.

8. The process of claim 1 wherein the oxidizing agent is selected from the group consisting of halogens, chloro, bromo, iodo or imides, hypervalent iodine compounds, perhalogen compounds, peroxide/halide combinations, sulfonyl halides, halo-hydantoins and N-halo compounds.

9. The process of claim 1 wherein the oxidizing agent is selected from the following:

1  Cl$_2$

2  Br$_2$

3  I$_2$

-continued

4: N-bromosuccinimide

5: N-chlorosuccinimide

6: N-iodosuccinimide

7: N-bromophthalimide

8: N-chlorophthalimide

9: N-bromosaccharin

10: N-chlorosaccharin

11: N-bromo-benzo[1,2,5]dithiazole 1,1,3,3-tetraoxide

12: N-chloro-benzo[1,2,5]dithiazole 1,1,3,3-tetraoxide

13: PhI(OCOCH₃)₂ derivative, R = H, COOH $$\text{CH}_3\text{COO}-\text{I}(\text{Ar})-\text{OCOCH}_3,\ \text{Ar} = o\text{-R-C}_6\text{H}_4,\ R = H,\ COOH$$

14: PhI(OCOCF₃)₂ derivative, R = H, COOH $$\text{CF}_3\text{COO}-\text{I}(\text{Ar})-\text{OCOCF}_3,\ R = H,\ COOH$$

15: NaOCl + HCl

16: NaOBr + HCl

17: NaOCl + HBr

18: $H_2O_2$ + HCl

19: $H_2O_2$ + KBr

20: 1,3-dibromo-5,5-dimethylhydantoin

21: 1-bromo-3-chloro-5,5-dimethylhydantoin

22: 1,3-dichloro-5,5-dimethylhydantoin

10. The process of claim 1 wherein the oxidation reaction is carried out at a temperature of from 15 to 150° C.

11. The process of claim 10 wherein the oxidation reaction is carried out at a temperature of from 60 to 100° C.

12. The process of claim 1 wherein the reaction is performed in an aprotic solvent.

13. The process of claim 12 wherein the solvent is selected from the group consisting of aprotic solvents that are basic.

14. The process of claim 12 wherein the aprotic solvent is selected from the group consisting of dimethyl formamide, dimethyl acetamide, pyridine, butyronitrile, chlorobenzene, 1,2-dichloroethane, toluene, acetic acid, dioxane, and ethylene glycol dimethyl ether.

15. A process for forming a 1H-pyrazolo (1,5-b)-[1,2,4]-triazole compound by ring closing a pyrazoloamidine as shown in the following equation:

wherein, $R^1$ and $R^2$ are independently selected alkyl or aryl groups;

Z is H or a substituent; and

OA/HAL represents an oxidizing agent that contains a halogen or a combination of an oxidizing agent and a halogen containing compound, the oxidizing agent having a reduction potential vs Ag/AgCl that is more positive than −0.16V and less than +1.43V.

16. The process of claim 15 wherein Z is Cl.

17. The process of claim 15 wherein $R^1$ is a tertiary carbon atom.

18. The process of claim 15 wherein $R^1$ is a t-butyl group.

19. The process of claim 15 wherein $R^2$ is a substituted alkyl or aryl group containing at least 8 carbon atoms.

20. The process of claim 15 wherein the reduction potential is in the range of from 0 to 1.0.

21. The process of claim 15 wherein the oxidizing agent is selected from the group consisting of halogens, chloroamides or imides, hypervalent iodine compounds, perhalogen compounds, peroxide/halide combinations, sulfonyl halides, halo-hydantoins and N-halo compounds.

22. The process of claim 15 wherein the reaction is performed in an aprotic solvent.

* * * * *